(12) United States Patent
Starr et al.

(10) Patent No.: US 6,699,203 B2
(45) Date of Patent: Mar. 2, 2004

(54) METHOD AND APPARATUS FOR DETERMINING CARDIAC OUTPUT

(75) Inventors: Eric W. Starr, Allison Park, PA (US); Bernard Pennock, Hilton Head Island, SC (US); Mouhyieldin Kandis, Haledon, NJ (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/172,271

(22) Filed: Jun. 14, 2002

(65) Prior Publication Data

US 2003/0013980 A1 Jan. 16, 2003

Related U.S. Application Data

(63) Continuation of application No. 09/691,595, filed on Oct. 18, 2000, now Pat. No. 6,413,226.
(60) Provisional application No. 60/161,120, filed on Oct. 22, 1999.

(51) Int. Cl.[7] .............................. A61B 5/08; A62B 7/00; A61M 16/00; F16K 31/02
(52) U.S. Cl. ................... 600/532; 600/538; 128/204.23
(58) Field of Search ............................. 600/532, 533, 600/538, 529, 526, 531, 508, 481; 128/204.18, 204.21, 204.22, 204.23

(56) References Cited

U.S. PATENT DOCUMENTS

| | | | |
|---|---|---|---|
| 5,494,031 A | 2/1996 | Hoefl | |
| 5,505,209 A | 4/1996 | Reining | |
| 5,971,934 A | 10/1999 | Scherer et al. | |
| 6,071,244 A | 6/2000 | Band et al. | |
| 6,098,622 A | 8/2000 | Nobile et al. | |
| 6,099,481 A | 8/2000 | Daniels et al. | |
| 6,106,480 A | 8/2000 | Gama De Abreu et al. | |
| 6,162,180 A | 12/2000 | Miesel et al. | |
| 6,186,955 B1 | 2/2001 | Baura | |
| 6,186,956 B1 | 2/2001 | McNamee | |
| 6,200,271 B1 | 3/2001 | Kuck et al. | |
| 6,210,342 B1 | 4/2001 | Kuck et al. | |
| 6,217,524 B1 | 4/2001 | Orr et al. | |
| 6,227,196 B1 | 5/2001 | Jaffe et al. | |
| 6,228,351 B1 | 5/2001 | Viders | |
| 6,238,351 B1 | 5/2001 | Orr et al. | |
| 6,241,681 B1 | 6/2001 | Haryadi et al. | |
| 6,251,082 B1 | 6/2001 | Rayburn | |
| 6,258,038 B1 | 7/2001 | Haryadi et al. | |
| 6,402,697 B1 | 6/2002 | Calkins et al. | |
| 6,406,435 B1 | 6/2002 | Mault | |

OTHER PUBLICATIONS

Novametrix Medical Systems, Inc., Technical Bulletin: Non–Invasive Cardiac Output (NICO), "Principles of Operation", 1998.

Novametrix Medical Systems, Inc., Non–Invasive Cardica Output (NICO), "Technology Review", 1999.

Capek et al., "Non–Invasive Measurement of Cardiac Output Using Partial CO2 Rebreathing", IEEE, 1998.

Jaffe, M.B., "Performance of a New "REBREATHING " Valve For Non–Invasive Cardiac Output Estimation", Novametrix Medical Systems.

(List continued on next page.)

Primary Examiner—Max F. Hindenburg
Assistant Examiner—Navin Natnithithadha
(74) Attorney, Agent, or Firm—Michael W. Haas

(57) ABSTRACT

A method and apparatus for use in determining the cardiac output. The method includes measuring a first parameter indicative of a patient's oxygen uptake and a second parameter indicative of the patient's fractional arterial oxygen concentration. The method also includes inducing a change in the patient's arterial oxygen concentration while taking these measurements to monitor the effects of the change in the patient's arterial oxygen concentration. The cardiac output is determined from the data collected regarding the effects of the change in the patient's arterial oxygen concentration.

25 Claims, 9 Drawing Sheets

OTHER PUBLICATIONS

Orr et al., "Clinical Validation of a New Non–Invasive Breath to Breath Fick Method for Cardiac Output Estimation", Novametrix Medical Systems, Inc.

Haryadi et al., "Influence of Error in Estimation of Intrapulmonary Shunt on the Measurement of Cardiac Output Using Rebreathing Techniques", University of Utah.

Haryadi et al., "Limited Reporducibility of Thermodilution Hampers Evaluation of New Cardiac Output Monitoring Devices", University of Utah.

Haryadi et al., "Clinical Evaluation of Partial CO2 Rebreathing Fick Technique for Non–Invasive Measurement of Cardiac Output", University of Utah.

Novametrix Medical Systems, Inc., "NICO Measures Cardiac Output Non–Inasively THrough Respiratory Gas Alalysis, Using A Partial CO2 Rebreathng Technique", Non–Invasive Cardiac Output (NICO).

Jaffe, M.B., "Partial Rebreathing Cardiac Output Overview", Novametrix Medical Systems, Inc., 1998.

Jaffe, M.B., "Development and Testing of a Cardiopulmonary Profile Monitor", Novametrix Medical Systems, Technical Report 9208 Rev. 00.

Gedeon et al., "A New Method for Non–Invasive Bedside Determination of Pulmonary Blood Flow", Medical & Biological Engineering & Computing, Jul. 1980.

Geddes et al., Principles of Applied Biomedical Instrumentation, 1968, USA.

METHOD AND APPARATUS FOR DETERMINING CARDIAC OUTPUT

CROSS REFERENCE TO RELATED APPLICATIONS

This application claims priority under 35 U.S.C. § 120 as a Continuation of U.S. patent appln. Ser. No. 09/691,595 filed Oct. 18, 2000 now U.S. Pat. No. 6,413,226, which claims priority under 35 U.S.C. § 119(e) from U.S. Provisional Patent Appln No. 60/161,120 filed Oct. 22, 1999.

BACKGROUND OF THE INVENTION

1. Field of the Invention

The present invention pertains to a method and apparatus for determining the cardiac output of a patient, and, more particularly, to a method of determining cardiac output by analyzing the effect that an induced change in the patient's arterial oxygen concentration has on their oxygen uptake and fractional arterial oxygen concentration, and to an apparatus for use in implementing such a method.

2. Description of the Related Art

There are several generally accepted techniques for measuring cardiac output (CO), which is the total volumetric flow of blood through the heart, and, thus, through the body at any given time. These techniques include: thermodilution, dye dilution, the direct Fick method, and partial $CO_2$ rebreathing. Thermodilution involves injecting cold saline directly into the right atrium of the heart and measuring the temperature change downstream in the pulmonary artery using a temperature sensor placed in this artery. Cardiac output is determined based on this temperature change versus time. Dye dilution is similar to thermodiluation except that a dye, rather than cold saline, is injected into the pulmonary artery. The amount of dye collected downstream is measured to determine the patient's cardiac output.

According to the direct Fick method, either the content of oxygen ($O_2$) or the content of carbon dioxide ($CO_2$) in both the arterial blood and mixed venous blood are measured. The Fick equation, written for oxygen, is: CO=$O_2$ uptake/(the content of $O_2$ in arterial blood—the content of $O_2$ in mixed venous blood). The Fick equation, written for carbon dioxide, is: CO=$CO_2$ excreted/(the content of $CO_2$ in mixed venous blood—the content of $CO_2$ in arterial blood). As noted above, the direct Fick method requires obtaining a mixed venous blood sample, which is only available in the pulmonary artery. See FIG. 1.

It can thus be appreciated that thermodilution, dye dilution, and the direct Fick method for determining cardiac output all require insertion of a catheter into the patient at, near, or through the heart. More specifically, in implementing these cardiac output measurements, a catheter is usually floated through the chambers of the heart in order to insert the saline or dye or to obtain the necessary blood sample at the correct location. For this reason, either of the above cardiac output measurement techniques is very invasive. Indeed, it is known that an arrhythmia may result from the placement of the catheter in or through the heart. Therefore, these cardiac output measurement techniques are typically only performed in the most critical of situations, where the need to know the patient's cardiac output outweighs the risk to the patient in taking this measurement.

The partial $CO_2$ rebreathing technique for measuring cardiac output, on the other hand, is a noninvasive approach believed to have been developed by Novametrix Medical Systems, Inc. of Wallingford, Conn. (Novametrix). This method is implemented using a device referred to as a NICO™ sensor, which is distributed by Novametrix. The NICO sensor measures the flow of gas to and from the patient and the $CO_2$ content in the patient's exhaled gas.

The partial $CO_2$ rebreathing cardiac output measurement technique is based on the $CO_2$ Fick equation in conjunction with what is called partial $CO_2$ rebreathing. According to this partial $CO_2$ rebreathing technique, cardiac output is measured by comparing the patient's $CO_2$ excretion to the arterial $CO_2$ content during normal breathing and during rebreathing, in which the patient rebreathes expired gases for a period of time. Cardiac output is determined as: CO=the change in $CO_2$ excretion/the change in the arterial $CO_2$ content.

Arterial $CO_2$ is typically determined from a sample of arterial blood. However, in order to eliminate the need for a blood sample to measure the arterial $CO_2$ content, the partial $CO_2$ rebreathing technique substitutes end tidal $CO_2$ ($ETCO_2$) for the required arterial $CO_2$ measurement. Therefore, the cardiac output equation becomes: CO=the change in $CO_2$ excretion/the change in the $ETCO_2$.

This partial $CO_2$ rebreathing technique, however, has several disadvantages. Namely, the patient is preferably intubated or breathing through a trachea tube when taking the flow and $CO_2$ measurements to capture the total volume of $CO_2$. In addition, the patient must be heavily sedated or unconscious so that he or she is not breathing spontaneously. If the patient is breathing spontaneously, the increased $CO_2$ level in the blood during the rebreathing phase would automatically trigger the patient's respiratory system to speed up or deepen the breaths to remove the excess $CO_2$. It is well known that for most patient's, the level of $CO_2$ is more important than the level of $O_2$ as a mechanism for triggering ventilation. Such a change in rate or depth of breathing prevents an accurate determination of cardiac output under this technique. It should also be noted that the use of end tidal $CO_2$, as opposed to the arterial $CO_2$ content, may introduce errors in determining cardiac output, because there are situations where the end tidal $CO_2$ may not correlate with the arterial $CO_2$ content. The partial $CO_2$ rebreathing cardiac output measurement technique is also disadvantageous because it does not adequately account for shunt blood flow, which is blood that is not oxygenated during the respiratory cycle. This flow cannot be directly measured, but must be estimated when using this conventional cardiac output measurement technique.

SUMMARY OF THE INVENTION

Accordingly, it is an object of the present invention to provide a method of measuring cardiac output that overcomes the shortcomings of conventional cardiac output measurement techniques. This object is achieved according to one embodiment of the present invention by providing a cardiac output measurement method that includes measuring a first parameter indicative of a patient's oxygen uptake and a second parameter indicative of the patient's fractional arterial oxygen concentration. The present method also includes inducing a change in the patient's arterial oxygen concentration and repeating these measurements to monitor the effects resulting from inducing the change in the patient's arterial oxygen concentration. The patient's cardiac output is determined based on the data collected.

It is yet another object of the present invention to provide an apparatus for non-invasively determining the cardiac output of a patient, including a spontaneously breathing patient, that does not suffer from the disadvantages associated with conventional cardiac measurement systems. This object is achieved by providing an apparatus that includes a system for measuring a first parameter indicative of a patient's oxygen uptake and means for measuring a second parameter indicative of the patient's fractional arterial oxygen concentration, such as a pulse oximeter. A processor determines the cardiac output based on the first parameter, and the second parameter. In addition, an output device outputs the result indicative of the patient's cardiac output.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
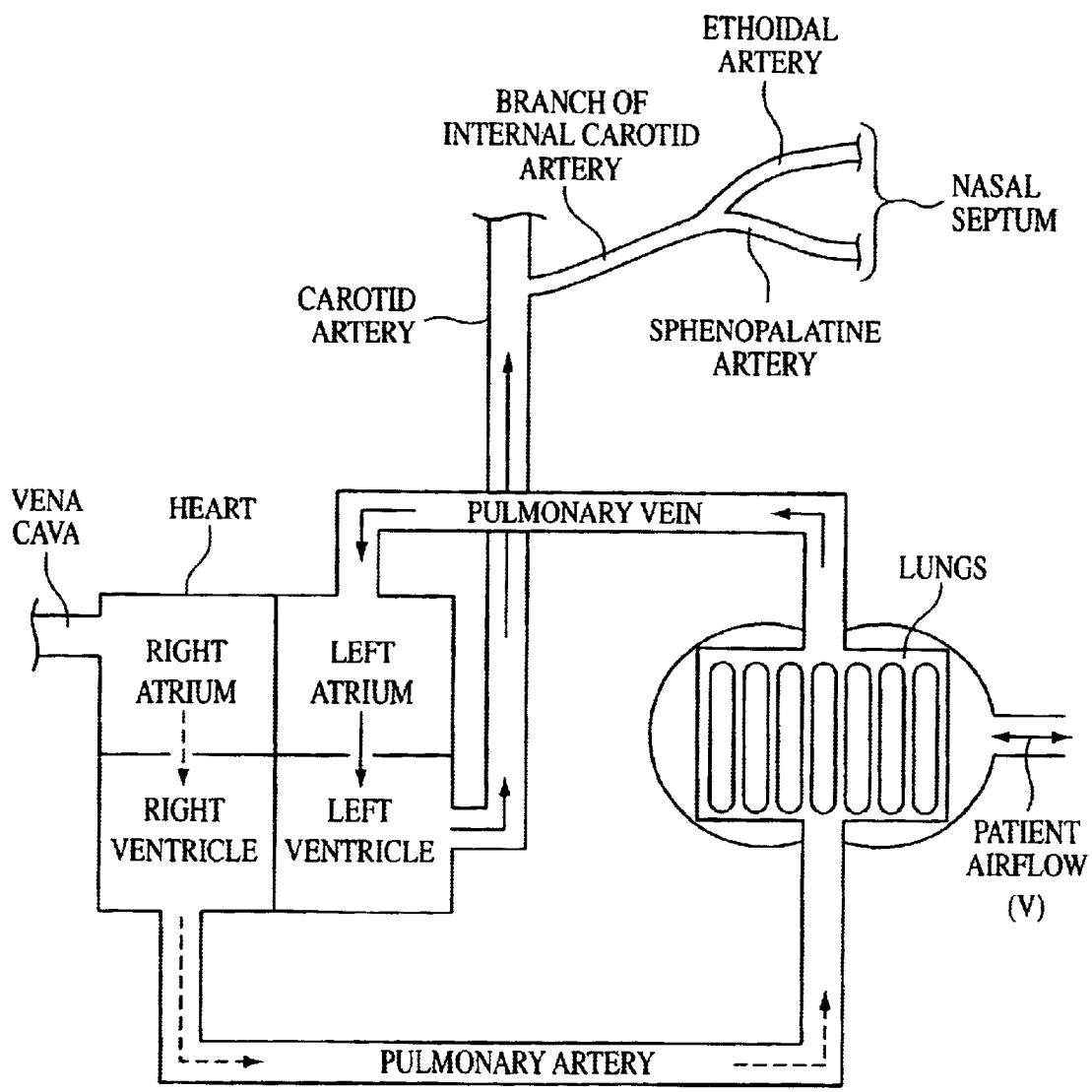
FIG. 1 is a schematic diagram of mammalian cardiopulmonary system.

FIG. 1 schematically illustrates a patient's cardiopulmonary system, which is useful in understanding the cardiac output measurement system of the present invention. The cardiac output measurement technique of the present invention measures the output, i.e., rate of flow of blood, from the left side of the heart. As described in detail below, the cardiac output measurement method of the present invention uses the transfer of oxygen from the lungs to the arteries in order to determine cardiac output.

The presently preferred method of determining the cardiac output includes the following steps, each of which is discussed in detail below:

(1) quantitatively measuring (a) a parameter indicative of the oxygen uptake of the patient, and (b) a parameter indicative of the patient's fractional arterial oxygen concentration ($XaO_2$);

(2) inducing a change in the patient's arterial oxygen concentration while taking measurements (a) and (b) set forth in step (1) to monitor the effects of the change in the patient's arterial oxygen concentration; and (3) from the data collected regarding the effect of the change in the patient's arterial oxygen concentration, determining the patient's cardiac output.

According to the present invention, the patient's cardiac output (CO) is determined based on the change in oxygen uptake versus the change in fractional arterial oxygen concentration resulting from the induced change in the arterial oxygen concentration. Stated another way:

$$CO = \frac{\text{change in the oxygen uptake}}{\text{change in the arterial oxygen concentration}}. \quad (1)$$

It is important to note that the patient's arterial oxygen concentration, not thier carbon dioxide concentration, is what is being manipulated in order to induce a change in the patient's oxygen uptake and fractional arterial oxygen concentration. As a result, this method can be performed on a spontaneously breathing patient, as well as on a patient who is not spontaneously breathing. Unlike changing the patient's $CO_2$ concentration, changing the patient's arterial $O_2$ concentration for a short time will not cause the patient to automatically attempt to alter their breathing pattern to move the $O_2$ concentration back to normal. Because this cardiac output measurement technique involves inducing a change in the patient's arterial oxygen concentration, it is referred to as an oxygen concentration modification cardiac output measurement method.

In one embodiment of the present invention, which is described in detail below, the patient's fractional arterial oxygen concentration is measured non-invasively using a conventional pulse oximeter. Thus, unlike conventional cardiac output measurement methods, the oxygen concentration modification cardiac output measurement method of the present invention can be performed non-invasively on a spontaneously breathing patient.

I. Measuring Airflow, Percent $O_2$ Inhaled/Exhaled, and the Fractional Arterial Oxygen Concentration According to the present invention, the patient's quantitative airflow and a parameter indicative of the percent oxygen inhaled and exhaled by the patient are measured to determine the patient's oxygen uptake. Oxygen uptake, also referred to as oxygen consumed by the patient, is the amount of oxygen absorbed into the blood in the lungs. It is typically expressed in liters as a volume $VO_2$ or in liters per minute (1 pm) as a volume flow rate $\dot{V}O_2$. Thus, equation (1) can be rewritten as follows:

$$CO \text{ (liters)} = \frac{\Delta(VO)_2}{\Delta XaO_2(T)}, \quad (2)$$

where T is a period over which the arterial oxygen concentration changes in response to a change in oxygen absorbed into the blood, as discussed in greater detail below with reference to FIG. 4). Equation (1) can also be rewritten as:

$$CO \text{ (lpm)} = \frac{\Delta \dot{V}O_2}{\Delta XaO_2}. \quad (3)$$

Oxygen uptake, which is measured during a breathing cycle, is determined by measuring the volumetric airflow $Q_{patient}$ to and from the patient, the % $O_2$ inhaled, and the % $O_2$ exhaled during that breathing cycle. Volumetric airflow is measured using a flow meter, such as a conventional pneumotach, that is capable of quantitatively measuring the flow of gas to and from the patient's airway. U.S. Pat. No. 6,017,315 to Starr et al., the contents of which are incorporated herein by reference, describes a suitable flow meter that quantitatively measures the flow of gas to and from a patient.

The % $O_2$ inhaled and % $O_2$ exhaled is measured using a conventional oxygen analyzer. An example of a combination flow sensing element and $O_2$ concentration analyzer window suitable for use in the present invention is taught in provisional U.S. patent application No. 60/170,918, the contents of which are incorporated herein by reference. More specifically, the present invention contemplates determining the % $O_2$ inhaled by measuring the patient's fraction of inspired oxygen ($FIO_2$) as a parameter indicative of the percent oxygen inhaled and exhaled, and multiplying this $FIO_2$ by 100, i.e., % $O_2$ inhaled=$FIO_2$ (inhaled) * 100. A similar process is used to determine % $O_2$ exhaled.

Oxygen uptake, $VO_2$, for one breath, is determined as follows:

$$(VO)_2 \text{inhaled} = \int_{t_1}^{t_2} (Q_{patient}[\%O_2/100]) dt, \quad (4)$$

$$(VO)_2 \text{exhaled} = \int_{t_2}^{t_3} (Q_{patient}[\%O_2/100]) dt, \text{ and} \quad (5)$$

$$VO_2 = VO_2 \text{inhaled} - VO_2 \text{exhaled}, \quad (6)$$

where $t_1$ is the start of inhalation, $t_2$ is the end of inhalation or start of exhalation, and $t_3$ is the end of exhalation. Oxygen uptake in liters per minute is then determined as:

$$\dot{V}O_2 = VO_2 * f_{breath}, \quad (7)$$

were $f_{breath}$ is the frequency of breaths, i.e., breaths per minute.

There are a variety of parameters indicative of fractional arterial oxygen concentration, $XaO_2$, of a patient that can be measured and used in the cardiac output determination method. One embodiment of the present invention contemplates measuring at least one of the following blood gas constituents, $SaO_2$, $PaO_2$, and $CaO_2$ as the parameter indicative of the patient's fractional arterial oxygen concentration $XaO_2$. These parameters are measured from an arterial blood sample or using a continuously indwelling catheter. It is preferable for one or more of these constituents to be measured continuously, for example, using an indwelling catheter so that the effects of the induced change in arterial oxygen concentration on the oxygen uptake and fractional arterial oxygen concentration can be monitored on a substantially continuous basis. This is especially important because of the relatively short duration of the effects of the induced change in arterial oxygen concentration resulting from the oxygen concentration modification step.

The present invention also contemplates measuring the pulse oximetry oxygen saturation level ($SpO_2$) of the patient as the parameter indicative of the fractional arterial oxygen concentration $XaO_2$. This measurement is advantageous in that the $SpO_2$ can be measured non-invasively using a conventional pulse oximeter. It can also be taken on a generally continuous basis to closely monitor the effects of the induced oxygen concentration modification on the patient's actual fractional arterial oxygen concentration.

Although the $SpO_2$ level can be taken from almost any location on the patient, such as the finger or ear, in a preferred embodiment, the $SpO_2$ is measured across the nasal septum. This location is especially desirable because it represents a relatively direct flow from the carotid artery, as shown in FIG. 1.

Depending on which parameter, $SpO_2$, $SaO_2$, $PaO_2$, or $CaO_2$, indicative of fractional arterial oxygen concentration $XaO_2$ is measured, a conversion may be required in order to arrive at the patient's actual fractional arterial oxygen concentration $XaO_2$. The only parameter indicative of fractional arterial oxygen concentration $XaO_2$ that does not have to be converted in order to arrive at the patient's fractional arterial oxygen concentration $XaO_2$ is the arterial oxygen content measurement $CaO_2$, because $CaO_2$ is a direct measurement of the fractional arterial oxygen concentration. Thus, $CaO_2 = XaO_2$, and no conversion is necessary.

Oxygen saturation, $SaO_2$, on the other hand, is not a direct measurement of the fractional arterial oxygen concentration $XaO_2$. If $SaO_2$ is the measured parameter, a conversion is needed, so that the measured $SaO_2$ can be used as the fractional arterial oxygen concentration $XaO_2$. For a normal adult, there is a linear relation between $SaO_2$ and $CaO_2$ and, hence, between $SaO_2$ and $XaO_2$. More specifically, the following relationship is known:

Vol % $O_2$=(Hb concentration)($O_2$ saturation ($SaO_2$) )($O_2$ carrying capacity of Hb), (8)

where, for a normal adult, the $O_2$ carrying capacity of hemoglobin (Hb) is approximately 1.34 $mlO_2$/gmHb, and the Hb concentration is approximately 15 gmHb/100 ml blood. Thus, for a normal adult:

$$XaO_2 = \frac{Vol\% O_2}{100} = \frac{15 \text{ gm Hb}}{100 \text{ ml bood}} * \frac{SaO_2}{100} * \frac{1.34 \text{ ml } O_2}{\text{gm HB}}. \quad (9)$$

Equation (9) can be simplified as:

$$XaO_2 = SaO_2 * k, \quad (10)$$

where, for a normal adult:

$$k = \frac{(15)(1.34)}{(100)(100)}. \quad (11)$$

Of course, the values for Hb concentration (15 gmHb) and $O_2$ carrying capacity of Hb (1.34 $mlO_2$) can differ depending on the individual. Therefore, if the Hb concentration and $O_2$ carrying capacity of Hb for an individual are known, a more exact relationship (k value) between $SaO_2$ and $XaO_2$ can be determined. The present invention contemplates that the values for Hb concentration and/or $O_2$ carrying capacity of Hb can be directly input by the user, automatically input from measurements taken by a co-oximeter or other equivalent device via a communication link with such a device, manually or automatically selected from a range of values based on information about the patient, or a default value can be used.

Figure 2:
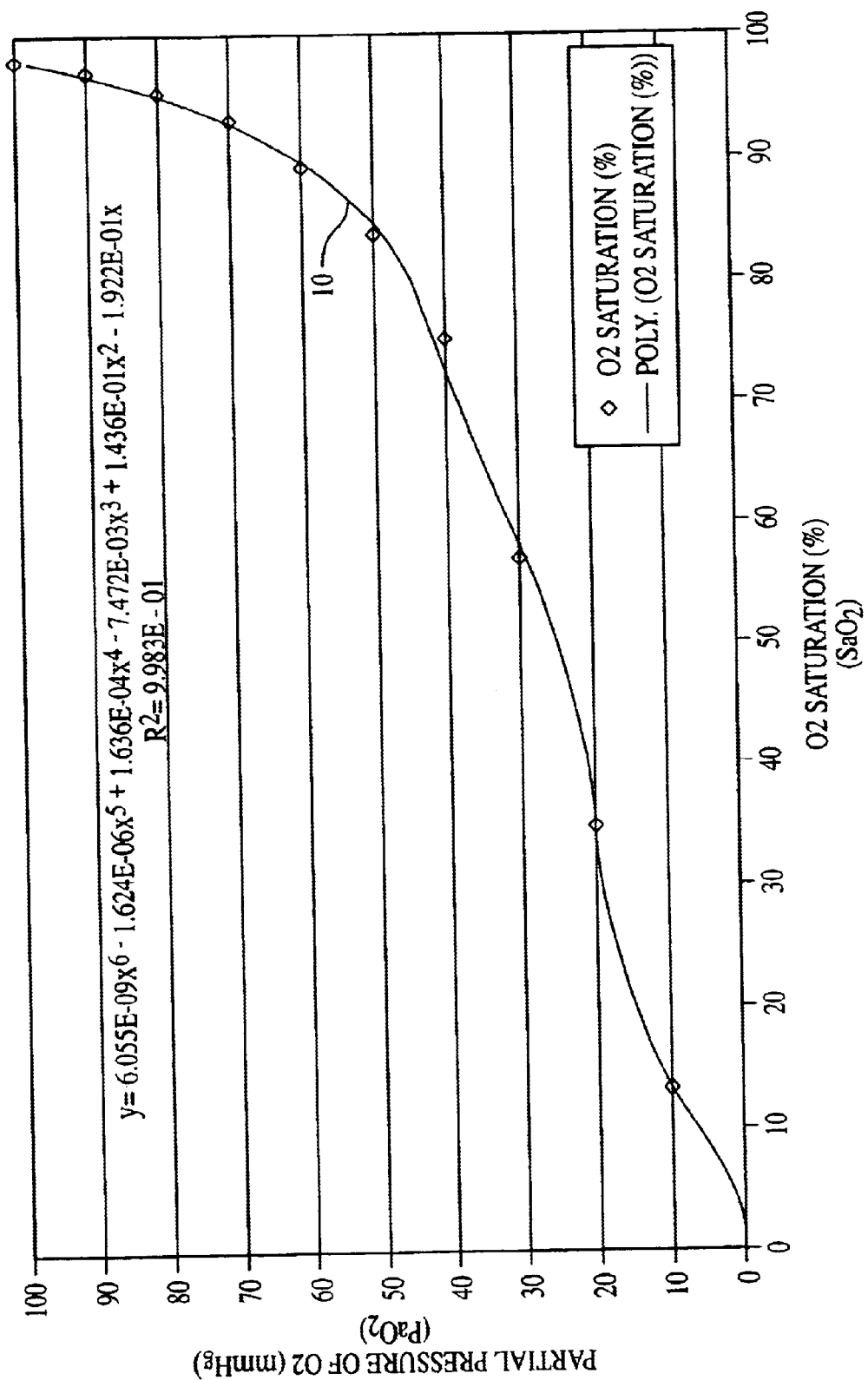
FIG. 2 is an oxygen-hemoglobin dissociation curve for a human.

There is also a known relationship, albeit nonlinear, between $PaO_2$ and $SaO_2$. This nonlinear relationship is graphically depicted in FIG. 2, which is referred to as an oxygen-hemoglobin dissociation curve 10. If $PaO_2$ is the measured parameter, it must first be converted to an $SaO_2$ using the dissociation curve, which can be accomplished using any conventional technique. Thereafter, the conversion factor k for $SaO_2$ must be used to arrive at the patient's fractional arterial oxygen concentration $XaO_2$ as discussed above.

A patient's $SaO_2$, $PaO_2$, or $CaO_2$ can only be measured by sampling the patient's arterial blood or using a continuously indwelling catheter, either of which is a relatively invasive procedure. $SpO_2$, on the other hand, which is an estimation of $SaO_2$, is measured non-invasively. Therefore, measuring the patient's $SpO_2$ has the advantage of being fast, easy, and non-invasive. If $SpO_2$ is taken as the measured parameter, it is considered an approximation of $SaO_2$, i.e., $SpO_2 \approx SaO_2$. Thus, the conversion factor k is applied to the measured $SpO_2$ to arrive at the patient's fractional arterial oxygen concentration $XaO_2$, i.e., $XaO_2 \approx SpO_2 * k$.

II. Inducing a Change in Arterial Oxygen Concentration

The present technique for determining a patient's cardiac output involves inducing a change the patient's arterial oxygen concentration. This can be done in a variety of ways, several of which are discussed below, so long as there is a measurable difference between the patient's baseline arterial oxygen concentration and the patient's arterial oxygen concentration following the induced change therein. Because the goal of this process is to force a change in the patient's arterial oxygen concentration, this step in the cardiac output measurement process of the present invention is referred to herein as the "oxygen concentration modification step."

It should be noted that the arterial oxygen concentration can either be increased or decreased depending on the condition of the patient. For example, a generally healthy patient has an oxygen saturation level of approximately 98%. As a result, there is very little room to improve oxygenation, e.g., up to 99%. Therefore, the present invention contemplates reducing the patient's oxygen saturation as one technique for inducing a change in the patient's arterial oxygen concentration, especially in those patients with a relatively high baseline $SaO_2$.

Reducing the patient's oxygen saturation can be accomplished by reducing the fraction of inspired oxygen ($FIO_2$) in the patient's inhaled gas. This can be accomplished, for example, by increasing the concentration of other inhaled gas constituents, such as nitrogen, which has the effect of lowering the patient's arterial oxygen saturation. In one embodiment of the present invention, the patient breathes nitrogen for one or more breaths, thereby reducing their arterial oxygen concentration. This technique is particularly suited for patients with a relatively high baseline oxygen concentration. This technique is particulary suited for patients with a relatively high baseline oxygen concentration.

As noted above, changing the patient's arterial oxygen concentration can also be accomplished by increasing the fraction of inspired oxygen in the inhaled gas. This can be accomplished, for example, by adding supplemental oxygen to the patient's inhaled gas, and, therefore, is particularly suited for patients with a relatively low baseline oxygen concentration.

The present invention also contemplates changing the patient's arterial oxygen concentration by having the patient rebreathe expired gas. However, because this will raise the patient's $CO_2$ level, this technique is best used on non-spontaneously breathing patients, where increased levels of $CO_2$ will not cause unusual breathing patterns. For a non-spontaneously breathing patient, the present invention also contemplates changing the arterial oxygen concentration by momentarily pausing the ventilator used to provide the patient's breathing.

Rebreathing expired gas can be used to change the patient's arterial oxygen concentration in a spontaneously breathing patient if steps are taken to minimize the increase in the patient's $CO_2$ level. For example, the carbon dioxide $CO_2$ is preferably is removed from the rebreathed gas so that the patient does not dramatically alter their breathing pattern due to rebreathing of exhaled carbon dioxide.

An exemplary embodiment of the present invention contemplates using a conventional $CO_2$ "scrubbing" technique for removing the $CO_2$ from the gas rebreathed by the patient. This is accomplished, for example, by placing a $CO_2$ scrubber in the rebreathing circuit or by passing the patient's exhaled gas through a $CO_2$ scrubber before it is returned to the patient. In either case, the rebreathed gas will have a lower oxygen concentration, thereby accomplishing the goal of changing the patient's arterial oxygen concentration without having the patient breathing $CO_2$, which will likely trigger a relatively rapid increase in the patient's breath rate.

III. Determining Cardiac Output

The present invention contemplates several techniques for calculating cardiac output based on the changes in oxygen uptake and the change in fractional arterial oxygen concentration resulting from the induced change in arterial oxygen concentration. Each of these techniques is discussed in turn below.

A. Technique 1—Calculating Cardiac Output Based on the Area Under the Curves

It is well known that the flow of fluid in a stream or conduit can be measured by monitoring a known mass or bolus of an indicator fluid downstream of where it was introduced into that stream. For example, it is known that the flow of fluid can be expressed as follows:

$$Flow = \frac{m}{cT} = \frac{\text{mass of indicator injected}}{\text{concentration of indicator} \times \text{time period of change in concentration}} \quad (12)$$

This relation is described, for example, by L. A. Geddes et al. in the textbook entitled, "Principles of Applied Biomedical Instrumentation", 3rd Edition, 1989, pages 576–578, and is the same principle used to measure cardiac output using the dye dilution technique.

The present invention contemplates introducing a bolus of non-oxygen into a patient's circulatory system as the indicator fluid rather than introducing a conventional dye. In other words, the present invention contemplates perturbing the cardio-respiratory system by removing a known volume of oxygen, which is referred to herein as introducing a bolus of non-oxygen into the system. Introducing a bolus of non-oxygen is equivalent to inducing a change in the patient's arterial oxygen concentration as discussed above. If the indicator fluid is a bolus or mass of non-oxygenated blood, the relationship described in equation (12) can be rewritten as follows:

$$CO = \frac{(VO_2)_{(bolus)}}{(\overline{X}_aO_2)(T)}, \qquad (13)$$

where CO is cardiac output, $VO_{2(bolus)}$ is the volume of non-oxygen taken up or absorbed by the blood in the lungs, i.e., the oxygen uptake of the non-oxygen bolus. T is the period over which the arterial oxygen concentration changes, i.e., a decrease in the illustrated embodiment, in response to the change in oxygen taken up by the patient (See FIG. 4), which is also a decrease in the illustrated embodiment. Finally, $\overline{X}_aO_2$ is the mean arterial oxygen concentration over period T.

Figure 3A:
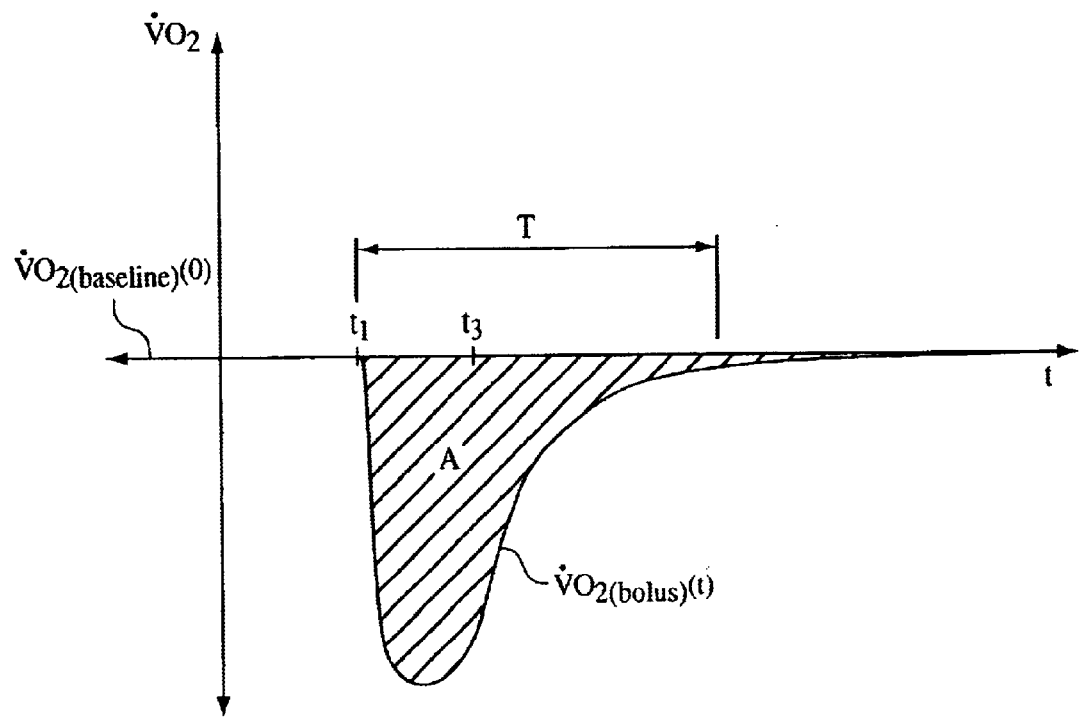
FIGS. 3A and 3B are graphs illustrating the change in oxygen uptake that takes place during an induced change in arterial oxygen concentration according to the cardiac output measurement method of the present invention.
Figure 3B:
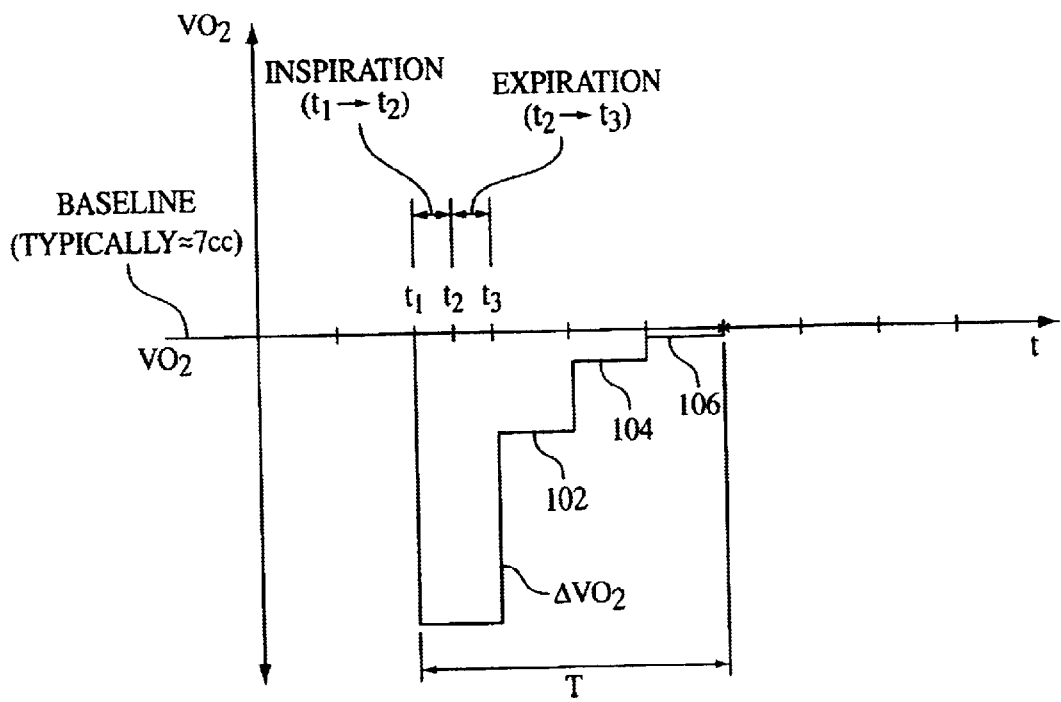

FIGS. 3A and 3B are graphs that illustrate the change in a patient's volume flow rate of oxygen taken in by the blood $\dot{V}O_2$ (FIG. 3A) and the change in oxygen uptake $VO_2$ (FIG. 3B) that takes place during the oxygen concentration modification step, in which a change in the arterial oxygen concentration, $XaO_2$, is induced using any of the above-described techniques. More specifically, FIGS. 3A and 3B illustrate the change in oxygen uptake that takes place by having the patient take one breath, i.e., from time $t_1$ to $t_3$, that is relatively devoid of oxygen. It should be noted that the change in oxygen uptake volume is illustrated in a step fashion in FIG. 3B because oxygen uptake is measured and calculated on a breath-by-breath basis. As shown in FIGS. 3A and 3B, it takes several breaths for the patient's oxygen uptake to stabilize back to its baseline level. Area A in FIG. 3A represents the change in the oxygen uptake $\Delta \dot{V}O_2$ the patient that occurs as a result of the oxygen concentration modification step. Similarly, FIG. 3B represents a histogram of the oxygen uptake volumes 100, 102, 104, and 106 resulting from the oxygen modification step.

Figure 4:
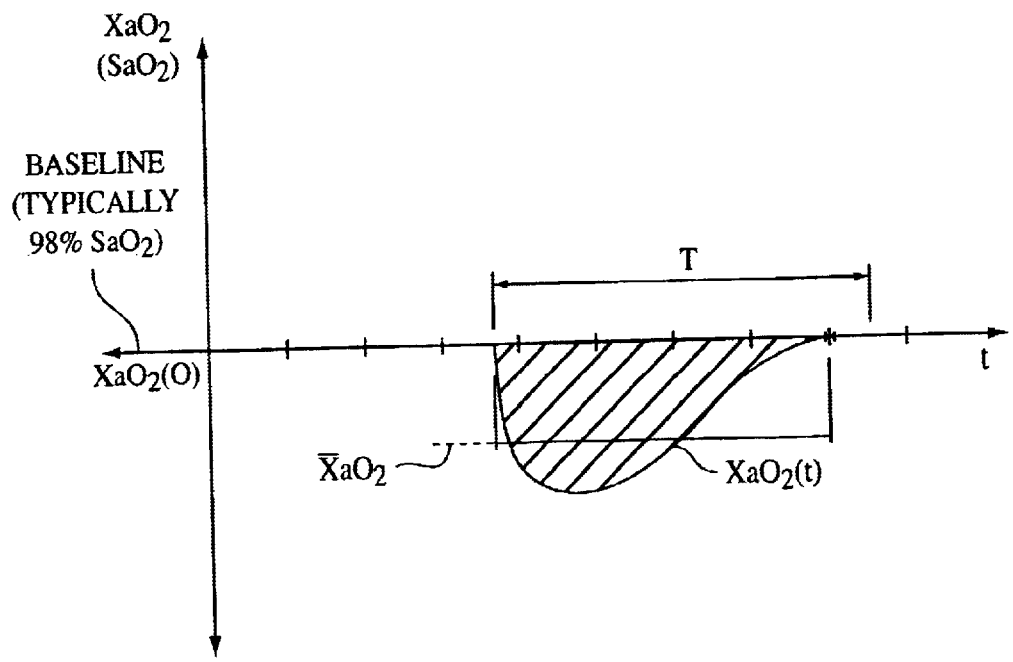
FIG. 4 is a graph illustrating the change in arterial oxygen saturation resulting from the induced change in arterial oxygen concentration.

FIG. 4 illustrates the change in arterial oxygen concentration $XaO_2$ resulting from the induced change in arterial oxygen concentration, which, in this embodiment, involves having the patient take one breath that is devoid of oxygen. In other words, FIG. 4 graphically shows the decrease in arterial oxygen concentration that occurs over time period T resulting from the oxygen concentration modification step shown in FIGS. 3A and 3B, which, in the present embodiment, is a decrease in the oxygen uptake.

The volume of non-oxygen taken by the patient's blood, $VO_{2(bolus)}$, which is shown as area A in FIG. 3A, can be calculated as follows:

$$VO_{2(bolus)} = \int_0^T \left[ \dot{V}O_{2(baseline)}(0) - \dot{V}O_{2(bolus)}(t) \right] dt, \qquad (14)$$

where $\dot{V}O_{2(baseline)}(0)$ is the baseline steady-state volume flow rate of oxygen taken up by the blood prior to the bolus injection, and $\dot{V}O_{2(bolus)}(t)$ is the volume flow rate of oxygen taken up by the blood after the bolus injection. It should be noted that period T in equation (14) can be the same a period T in FIG. 4, or it can be a different period, so long as the function of calculating the volume of non-oxygen taken up by the blood is substantially met, i.e., area A is calculated to a close approximation.

The mean arterial oxygen concentration, $\overline{X}_aO_2$, which is shown in FIG. 4, can be calculated as follows:

$$\overline{X}_aO_2 = \frac{1}{T} \int_0^T [X_aO_2(0) - X_aO_2(t)] dt, \qquad (15)$$

where $X_aO_2(0)$ is the baseline steady-state arterial oxygen concentration prior to the bolus injection, and $X_aO_2(t)$ is the arterial oxygen concentration after the bolus injection.

Combining equations (14) and (15) into equation (13) yields:

$$CO = \frac{\int_0^T \left[ \dot{V}O_{2(baseline)}(0) - \dot{V}O_{2(bolus)}(t) \right] dt}{\int_0^T [X_aO_2(0) - X_aO_2(t)] dt}, \qquad (16)$$

Thus, a patient's cardiac output can be estimated by monitoring the patient's oxygen uptake any conventional technique and by measuring a parameter indicative of the patient's fractional arterial oxygen concentration $(XaO_2)$ before and after a bolus of non-oxygen is introduced into the patient's system, which has the effect of altering the patient's arterial oxygen concentration.

It can be appreciated that the expression $\dot{V}O_{2(baseline)}(0) - \dot{V}O_{2(bolus)}(t)$ in the numerator in equation (16) represents the change in the volume flow rate of oxygen taken up by the blood relative to the baseline steady-state volume flow rate. In the example shown in FIGS. 3A and 3B, this change is shown as a lowering of the volume flow rate of consumed oxygen, i.e., dipping of the $\dot{V}O_{2(bolus)}(t)$ curve below the baseline, because in this example, the patient was presented with a bolus of non-oxygen, e.g., by reducing the $FIO_2$.

However, the present invention also contemplates presenting the patient with a bolus of increased oxygen, e.g., by increasing the $FIO_2$. The result will be an increase in the volume flow rate of consumed oxygen, i.e., a increase of the $\dot{V}O_{2(bolus)}(t)$ curve above the baseline. In which case, the change in the volume flow rate of oxygen taken by the blood relative to the baseline steady-state volume flow rate in equation (16) can be expressed as follows:

$$VO_{2(bolus)} = \int_0^T \left[ \dot{V}O_{2(bolus)}(t) - \dot{V}O_{2(baseline)}(0) \right] dt. \qquad (17)$$

This would similarly cause the change in arterial oxygen concentration to appear as in increase over the baseline value so that equation (16) can be expressed as:

$$\overline{X}_aO_2 = \frac{1}{T} \int_0^T [X_aO_2(t) - X_aO_2(0)] dt, \qquad (18)$$

Thus, as before, we can substitute equations (17) and (18) into equation (13) to get:

$$CO = \frac{\int_0^T \left[ \dot{V}O_{2(bolus)}(t) - \dot{V}O_{2(baseline)}(0) \right] dt}{\int_0^T [X_aO_2(t) - X_aO_2(0)] dt}. \qquad (19)$$

Equation (19) represents situations where the patient receives an increased level of oxygen as a means to alter the arterial oxygen concentration. It should be noted, however, that equation (16) is suitable for either situation, because the signs in the numerator and denominator would cancel where there is an increase over the baseline value.

It can be further appreciated that the numerator in equation (13) represents by the sum of the volumes $VO_2$ in the histogram shown in FIG. 3B. That is, summing volumes indicated by levels 100, 102, 104 and 106 yields an indication of the total volume of non-oxygen taken in by the blood. Thus, equation (13) can be rewritten as:

$$CO = \frac{\sum_{0}^{T} \Delta VO_2}{\overline{X_aO_2} * T}, \qquad (20)$$

where $$\sum_{0}^{T} \Delta VO_2$$

represents the sum of the bars of the histogram during period T (which is determined as discussed above with respect to FIG. 4). Substituting equation (15) into equation (20) allows equation (20) to be rewritten as:

$$CO = \frac{\sum_{0}^{T} \Delta VO_2}{\int_{0}^{T}[X_aO_2(0) - X_aO_2(t)]dt}. \qquad (21)$$

Either technique: 1) integrating curve $\dot{V}O_{2(bolus)}(t)$ over period T (FIG. 3A, equations (16) and (19)), or 2) summing the changes in volume of oxygen taken in by the blood $\Delta VO_2$ over period T (FIG. 3B, equations (20) and (21)) provides an estimation of cardiac output.

Figure 5A:
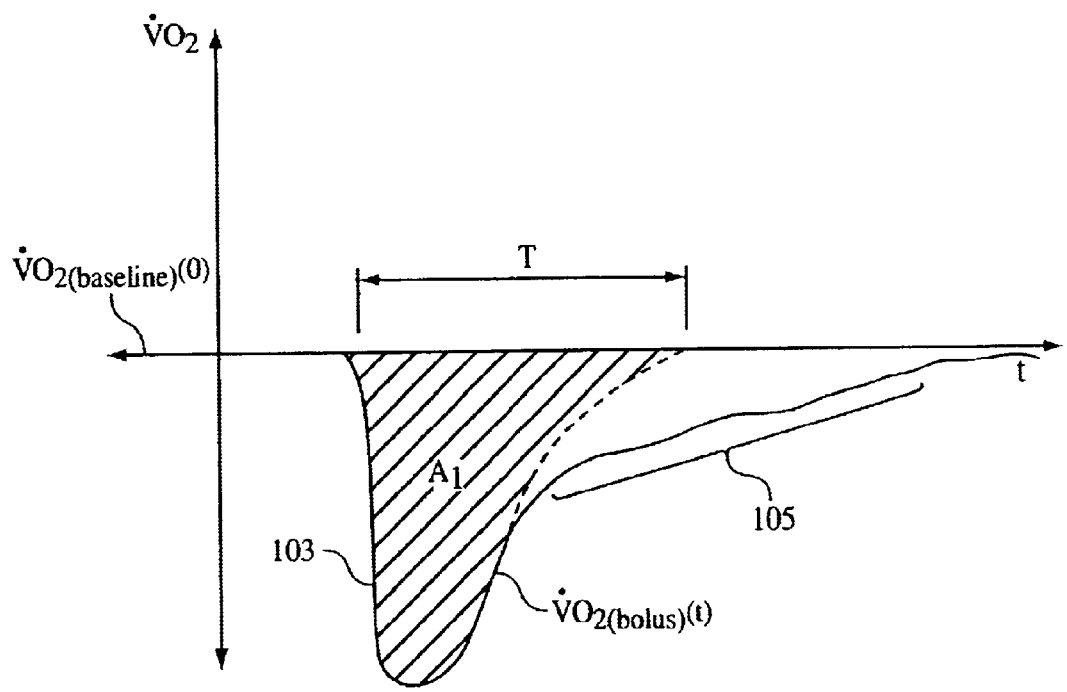
FIGS. 5A and 5B are graphs illustrating the change in oxygen uptake resulting from the induced change in arterial oxygen concentration including the potential effects of recirculation.
Figure 5B:
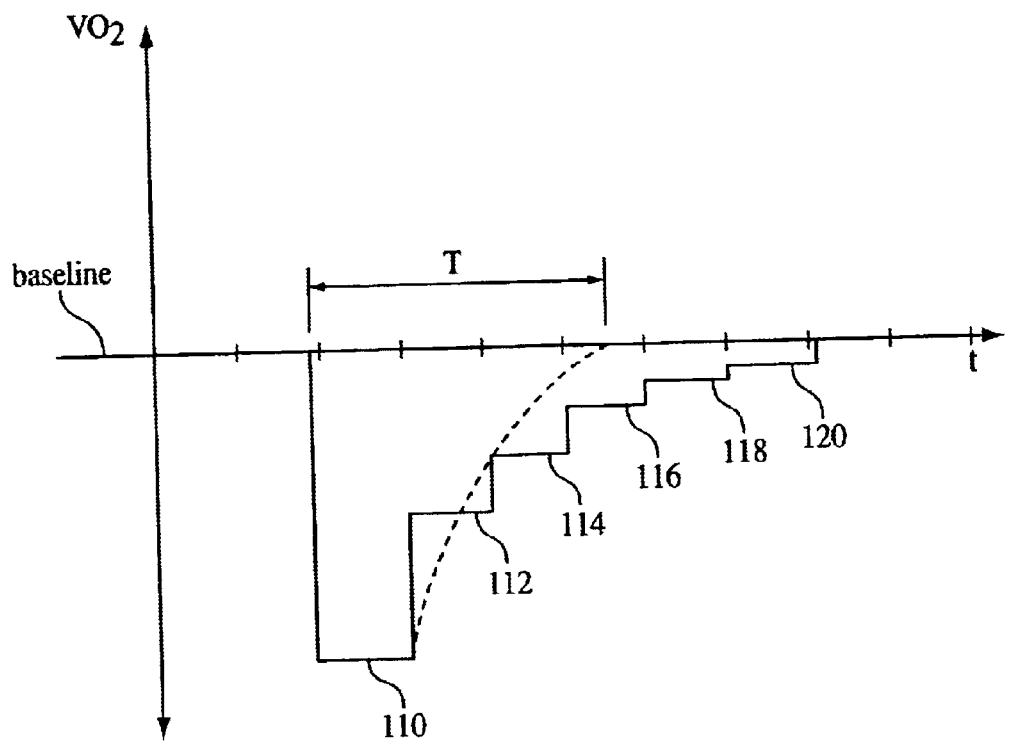
Figure 6:
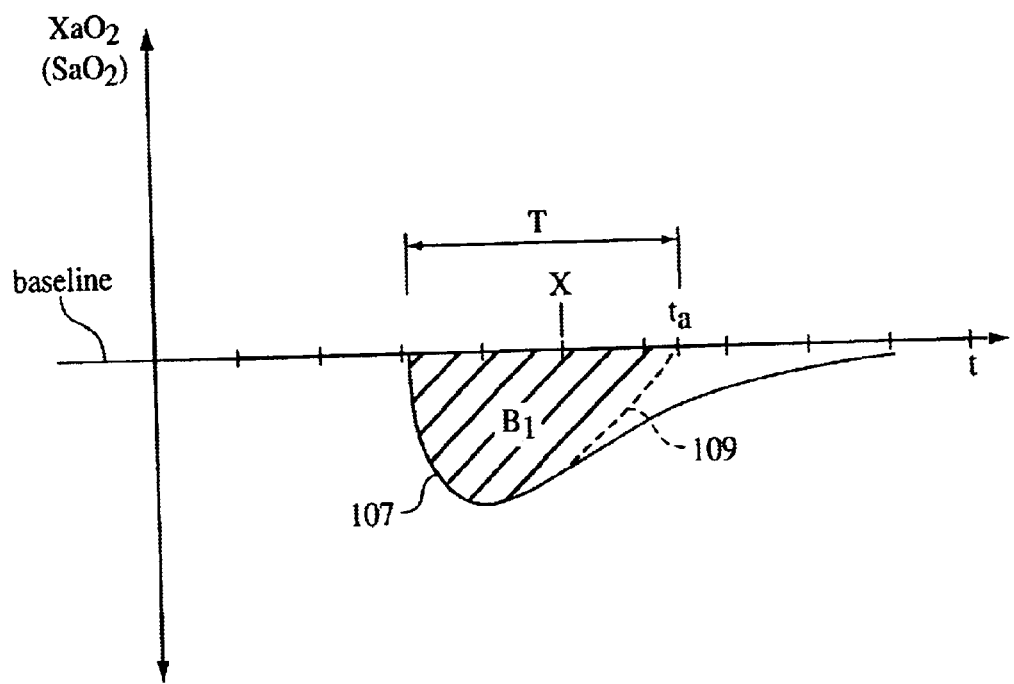
FIG. 6 is a graph illustrating the change in arterial oxygen concentration resulting from the induced change in arterial oxygen concentration including the potential effects of recirculation.

FIGS. 5A, 5B, and 6 are similar to FIGS. 3A, 3B, and 4, respectively, except that FIGS. 5A, 5B, and 6 take into consideration a scenario in which the bolus of oxygen or non-oxygen in the patient's blood begins to recirculate at time x during the oxygen concentration modification step. As shown in FIG. 5A, recirculation will cause the volume flow rate of oxygen taken by the blood $\dot{V}O_{2(bolus)}(t)$, i.e., curve 103, to move toward the baseline level slower than if there was no recirculation, as indicated by portion 105 of curve 103. Similarly, as shown in FIG. 5B, the volume of oxygen taken in by the blood $VO_2$ will also move toward the baseline level more slowly. This can be appreciated by comparing FIG. 5A to 3A and FIG. 5B to FIG. 3B. As shown in FIG. 6, the arterial oxygen concentration $XaO_2$ curve 107 will also move toward the baseline, steady-state level more slowly than in the absence of recirculation.

The present invention contemplates dealing with the effects of recirculation by estimating time period T for use in the above cardiac output calculations. Estimating T involves extrapolating curve 107 using conventional extrapolation techniques, as shown by dashed line 109, to determine an extrapolated time $t_a$ when the arterial oxygen concentration returns to the base line level. T is then determined from the start of the change in arterial oxygen concentration to time $t_a$, as shown in FIG. 6. This time period T based on extrapolation is then used, as shown in FIG. 5A to solve equation (15), or as shown in FIG. 5B to solve equation (19). For example, the consumed oxygen volumes corresponding to levels 110, 112 and 114 would be used in solving equation (19), while levels 116, 118 and 120 would not.

B. Technique 2—Calculating Cardiac Output

In another formulation for cardiac output, we start with the simple relationship between the volume of oxygen contained in an arbitrary volume of flowing blood. The oxygen volume can be evaluated as:

$$\Delta VO_2 = (\Delta X_aO_2)(\Delta V), \qquad (22)$$

If we solve for total blood volume, equation (22) becomes $$\Delta V = \frac{\Delta VO_2}{\Delta X_aO_2}, \qquad (23)$$

We will assume that the volume of oxygen in the numerator of (23) is simply the oxygen taken up by the blood as measured at the airway. This is simply:

$$\Delta VO_2 = VO_2(t_{start}) - VO_2(t_{end}), \qquad (24)$$

where $t_{start}$ is the volume at an arbitrary starting point on the volume time curve of airway oxygen and $t_{end}$ is the volume at some point in time after $t_{start}$.

The change in arterial oxygen concentration can then simply be written as:

$$\Delta X_aO_2 = X_aO_2(t'_{start}) - X_aO_2(t'_{end}), \qquad (25)$$

where $t'_{start}$ is the temporal location in the concentration curve that corresponds physically to $t_{start}$ and $t'_{end}$ is the temporal location in the concentration curve that corresponds physically to $t_{end}$.

Substituting equations (24) and (25) into (23), we have $$\Delta V = \left[\frac{VO_2(t_{start}) - VO_2(t_{end})}{X_aO_2(t'_{start}) - X_aO_2(t'_{end})}\right], \qquad (26)$$

Because equation (26) represents the volume of blood, we can calculate the cardiac output as:

$$CO = \frac{\Delta V}{t'_{end} - t'_{start}}, \qquad (27)$$

Note that because cardiac output is the flow of blood, we must use the time span associated with the flowing blood, $t'_{end} - t'_{start}$.

Finally, substituting equation (26) into equation (27), we have:

$$CO = \left[\frac{1}{t'_{end} - t'_{start}}\right]\left[\frac{VO_2(t_{start}) - VO_2(t_{end})}{X_aO_2(t'_{start}) - X_aO_2(t'_{end})}\right]. \qquad (28)$$

Figure 7:
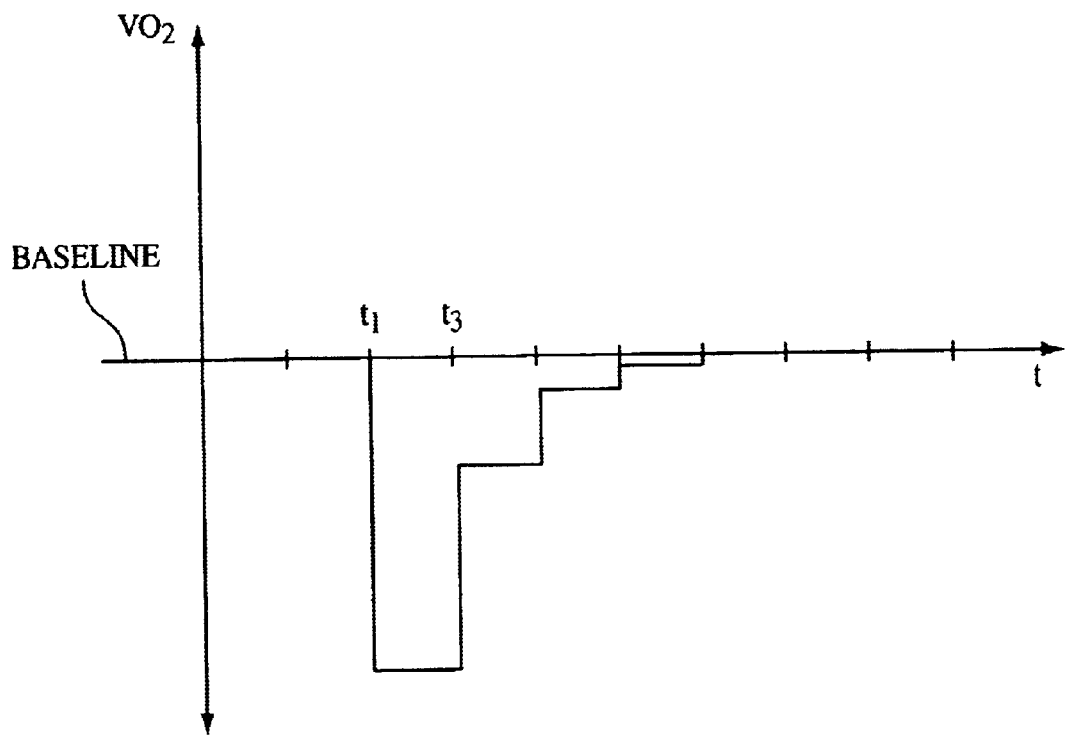
FIGS. 7 and 8 are graphs illustrating the change in oxygen uptake and arterial oxygen concentration, respectively, resulting from the induced change in arterial oxygen concentration illustrating an alternative embodiment for determining cardiac output based on these changes.
Figure 8:
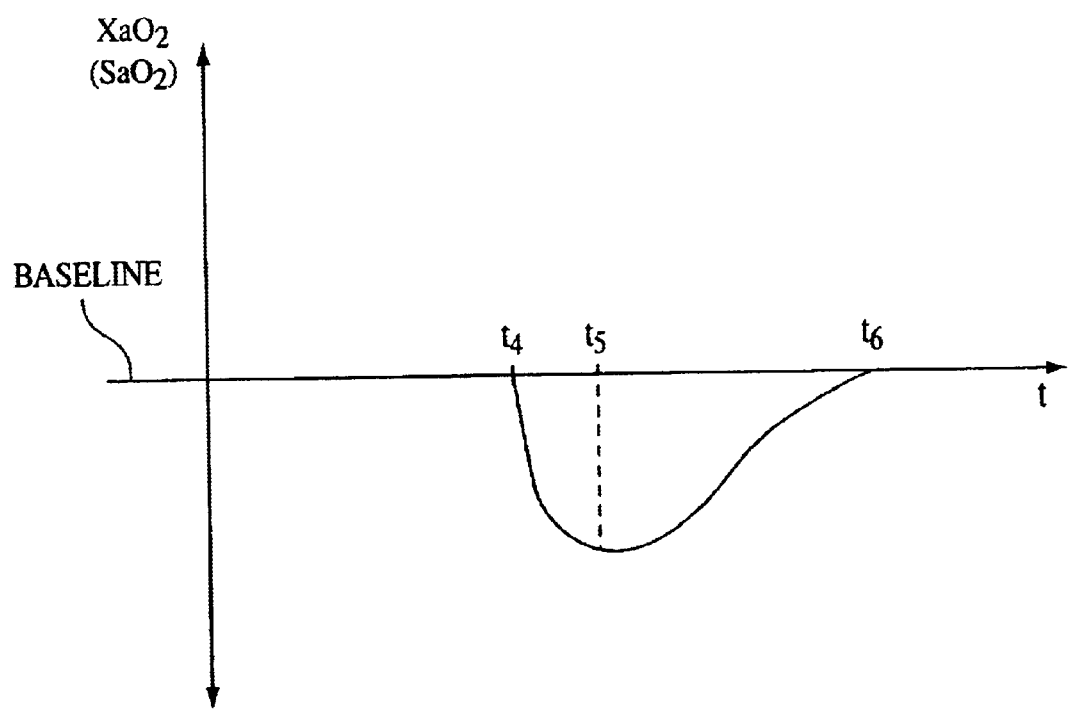

Referring now to FIGS. 7 and 8, for example, $t_{start}$ corresponds to point $t_1$, $t'_{start}$ corresponds to point $t_4$, $t_{end}$ is arbitrarily selected for illustration purposes as $t_3$, and $t'_{end}$ therefore correspond to point $t_5$. Thus, cardiac output can be determined as:

$$CO = \left[\frac{1}{t_5 - t_4}\right]\left[\frac{VO_2(t_1) - VO_2(t_3)}{X_aO_2(t_4) - X_aO_2(t_5)}\right]. \qquad (29)$$

C. Technique 3—Calculating Cardiac Output Based on the Magnitude of the Curves

Figure 9:
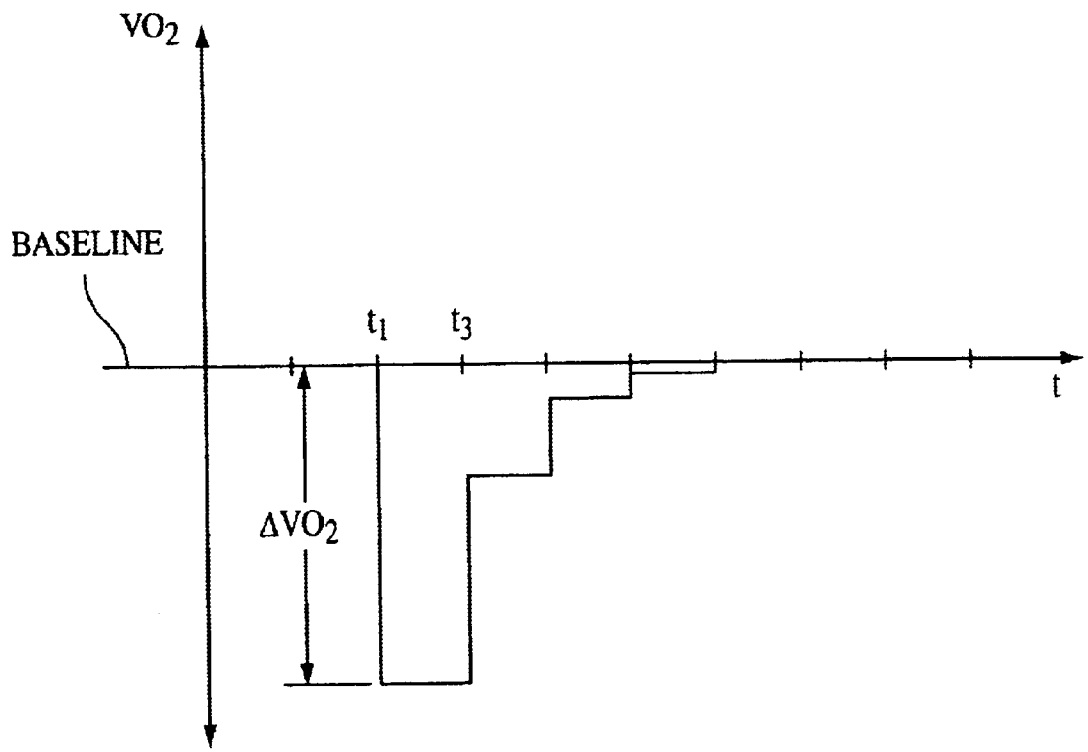
FIGS. 9 and 10 are graphs illustrating the change in oxygen uptake and arterial oxygen concentration, respectively, resulting from the induced change in arterial oxygen concentration illustrating yet another alternative embodiment for determining cardiac output based on these changes.
Figure 10:
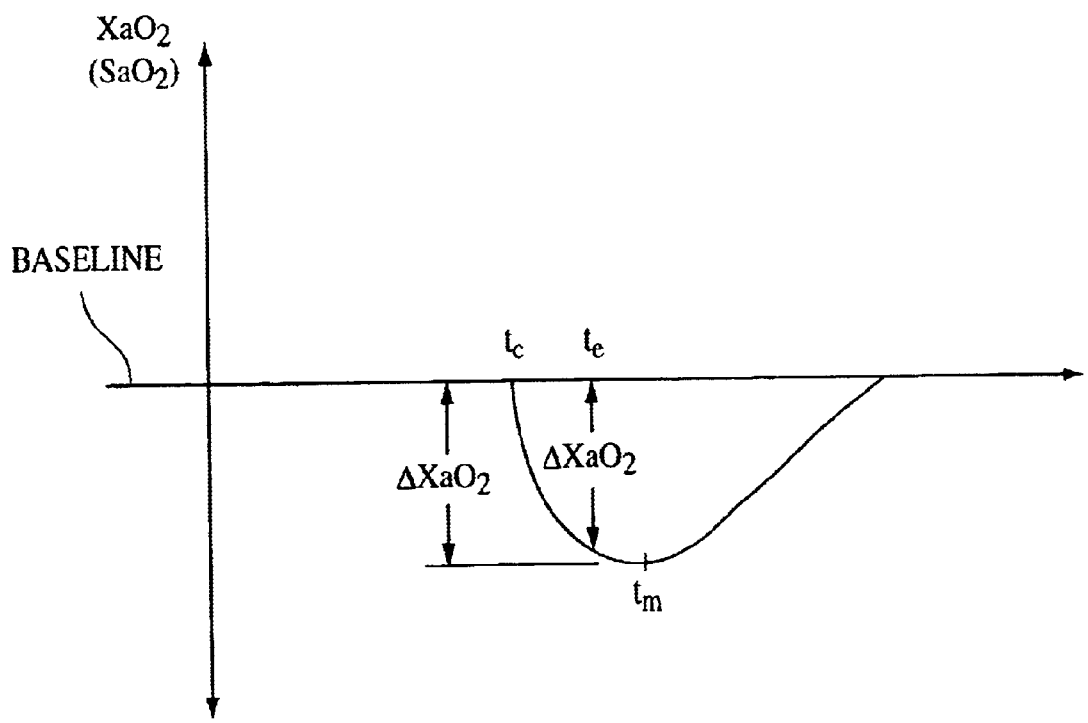

Yet another technique for determining cardiac output involves comparing the magnitude of the change in oxygen uptake with the magnitude of the change in arterial oxygen concentration resulting from the oxygen concentration modification step. FIGS. 9 and 10 illustrate the changes in the patient's oxygen uptake and arterial oxygen saturation, respectively, resulting from the oxygen concentration modification step. From FIG. 9, it can be appreciated that there is a relatively large initial drop in oxygen uptake at the start of the oxygen concentration modification step, i.e., from time $t_1$ to $t_3$. The magnitude of this drop can be determined from the output of the flow sensor and the oxygen analyzer using any conventional technique. From FIG. 10, it can be appreciated that there is a corresponding drop in arterial oxygen saturation. Although, as noted above, this drop in arterial oxygen concentration is delayed in time from the initial drop in oxygen uptake. This drop begins at time $t_c$ and reaches a maximum difference from the initial baseline level at time $t_m$. The value of the fractional arterial oxygen concentration at $t_m$, $XaO_2(t_m)$, can be determined using any conventional technique.

As a side note, it is worth remembering that the oxygen concentration modification step also contemplates increasing the patient's arterial oxygen in some situations. In which case, the change in oxygen uptake will be in the positive direction, opposite that shown in FIGS. 3A, 3B, 5A, 5B, 7, and 9. Similarly, the change in the fractional arterial oxygen concentration will also be in the positive direction, opposite that shown in FIGS. 4, 6, 8, and 10. The techniques for determining cardiac output discussed herein are equally applicable where the oxygen concentration modification step is performed by increasing the patient's arterial oxygen.

Referring again to FIGS. 9 and 10, one embodiment of the present invention contemplates comparing the magnitude of the change in oxygen uptake from time $t_1$ to $t_3$ with the magnitude of the change in arterial oxygen concentration from time $t_c$ to $t_m$, so that the patient's cardiac output is defined as:

$$CO = \frac{\Delta \dot{V}O_2(\text{Magnitide } t_1 \text{ to } t_3)}{\Delta XaO_2(\text{Magnitide } t_c \text{ to } t_m)}. \tag{30}$$

It can be appreciated that equation (22) represents a direct calculation for cardiac output because the units represented by the numerator are, for example, liters/second or liters/minute, and the denominator is unitless.

Another embodiment of the present invention contemplates determining cardiac output based on the time period $t_c$ to $t_e$, where $t_c$ to $t_e=t_1$ to $t_3$, so that $$CO = \frac{\Delta \dot{V}O_2(\text{Magnitide } t_1 \text{ to } t_3)}{\Delta XaO_2(\text{Magnitide } t_c \text{ to } t_e)}. \tag{31}$$

As with equation (30), equation (31) also represents a direct calculation for cardiac output because the units represented by the numerator are, for example, liters/second or liters/minute, and the denominator is unitless. In these embodiments, the change in magnitude of the oxygen uptake and fractional arterial oxygen concentration are monitored during the oxygen modification step, which is why this technique is referred to in the preceding section heading as the "Magnitude of the Curve" technique.

The determination of cardiac output using equations (30) or (31) can also be understood by referring back to equation (16). That is, equation (16) can be readily derived to arrive at equation (30) or (31). For example, if equation (16) is adjusted by multiplying the denominator across the expression we have:

$$CO \int_0^T [X_aO_2(0) - X_aO_2(t)]dt = \tag{32}$$

-continued
$$\int_0^T [\dot{V}O_{2(baseline)}(0) - \dot{V}O_{2(bolus)}(t)]dt.$$

Differentiating both sides of equation (32) with respect to time yields the following expression:

$$CO[X_aO_2(0)-X_aO_2(t)]=[\dot{V}O_{2(baseline)}(0)-\dot{V}O_{2(bolus)}(t)], \tag{33}$$

which can be rewritten as:

$$CO = \frac{[\dot{V}O_{2(baseline)}(0) - \dot{V}O_{2(bolus)}(t)]}{[X_aO_2(0) - X_aO_2(t)]}. \tag{34}$$

It can be appreciated that equation (34) corresponds to equations (30) and (31), where $\Delta \dot{V}O_2$ in equation (30) or (31) is equal to the expression $\dot{V}O_{2(baseline)}(0)-\dot{V}O_{2(bolus)}(t)$ in equation (34), and where $\Delta XaO_2$ in equations (30) and (31) is equal to the expression $X_aO_2(0)-X_aO_2(t)$ in equation (34), except that specific times $t_m$ or $t_e$ are used in equations (30) and (31) in place of $\dot{V}O_{2(bolus)}(t)$ in equation (34).

One embodiment of the present invention contemplates determining the baseline oxygen uptake and baseline arterial oxygen concentration before performing the oxygen concentration modification step so that the changes in oxygen uptake and baseline arterial oxygen concentration resulting from the oxygen concentration modification step can be compared to this baseline. It is to be understood, however, that in an alternative embodiment of the present invention, the baseline oxygen uptake and baseline arterial oxygen concentration are established after the effects of the oxygen concentration modification step; namely, after the patient's cardio-pulmonary system has returned to a steady state following the oxygen concentration modification step.

Figure 11:
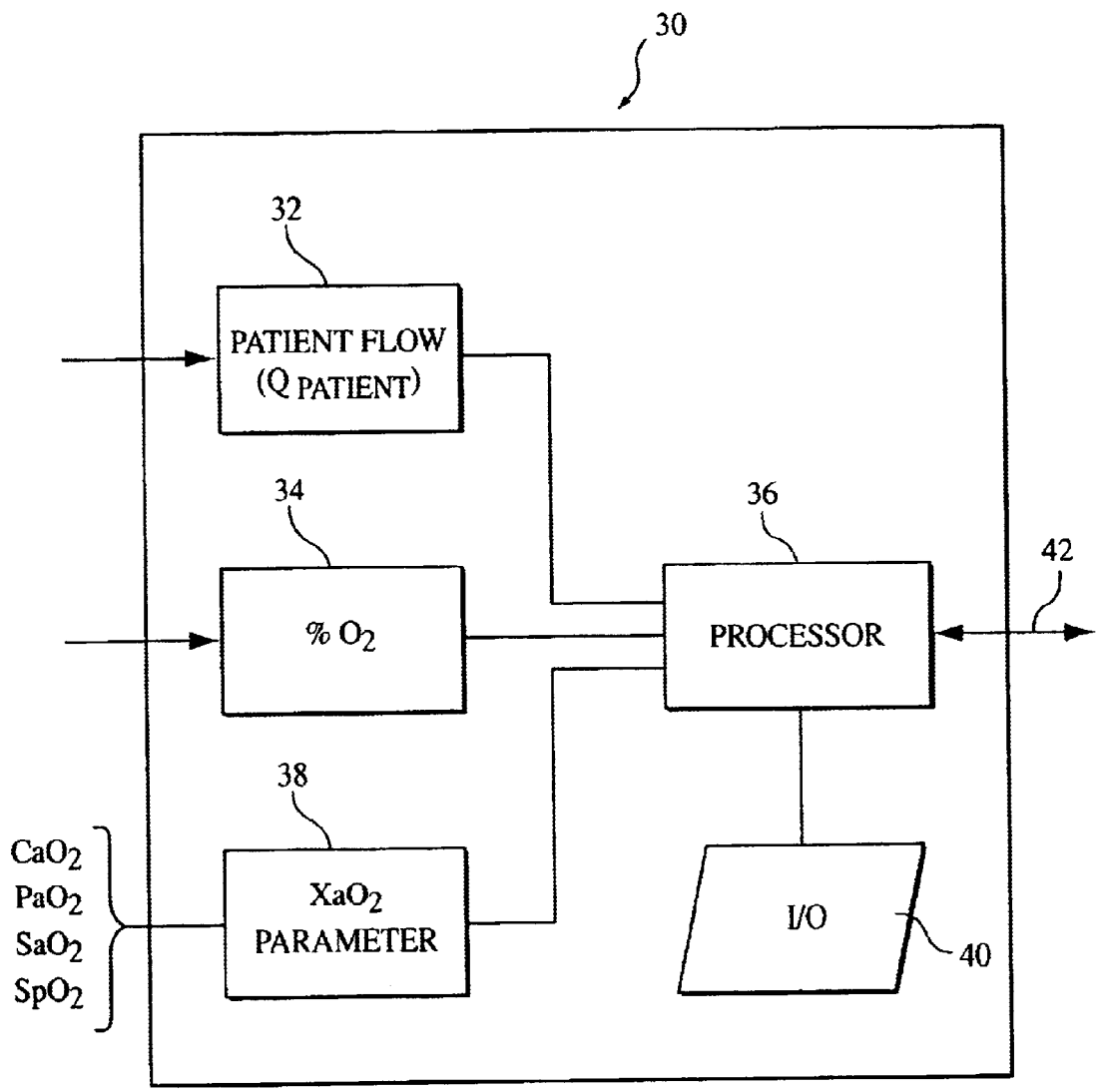
FIG. 11 is a schematic diagram of a device for implementing the cardiac output measurement method of the present invention.
Figure 12:
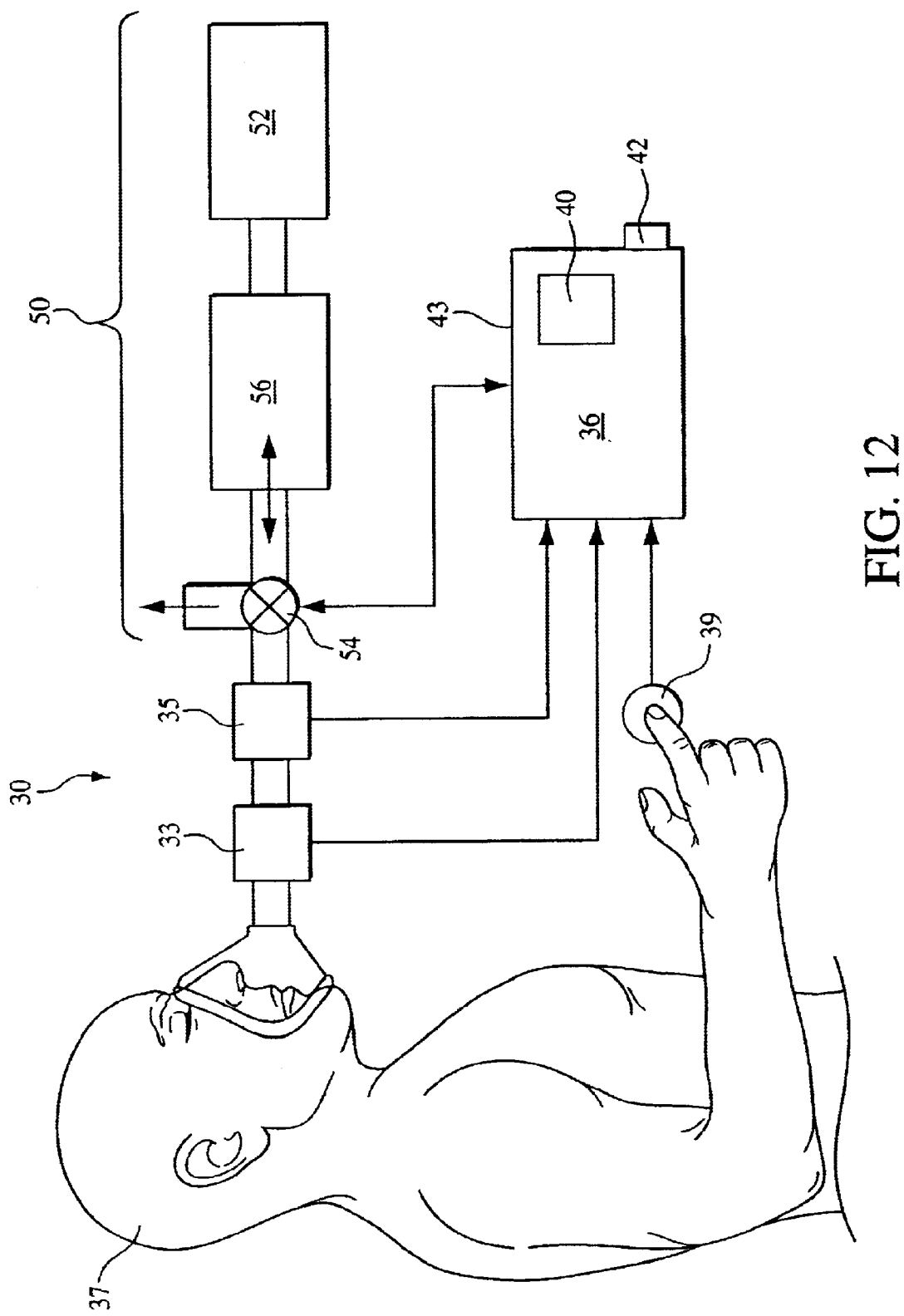
FIG. 12 is a schematic diagram of the device of FIG. 11 shown in use on a patient.

FIGS. 11 and 12 schematically illustrate an exemplary embodiment of a cardiac output measurement device 30 used to implement the above-described cardiac output measurement method. Cardiac output measurement device 30 includes a patient flow measurement system 32 for quantitatively measuring the flow of gas to and from the patient and an oxygen analyzer 34 that measures the patient's fraction of inspired oxygen ($FIO_2$). Patient flow measurement system 32 includes a flow sensor 33, also referred to as a flow element, that creates a pressure differential for measuring the flow of gas passing through the flow element. Oxygen analyzer 34 includes an oxygen analyzing element 35, which is essentially an airway adapter optical window and an $O_2$ transducer having phototransmitter and photodector, that is used to measure the amount of oxygen passing in front of the optical window. Flow sensor 33 and oxygen analyzing element 35 are preferably located proximate to the patient's airway. The outputs of the patient flow and oxygen analyzing systems are provided to a microprocessor 36 for calculating the patient's oxygen uptake.

Cardiac output measurement device 30 includes means 38 for detecting a parameter indicative of the fractional arterial oxygen concentration, $XaO_2$, of a patient. As noted above, this parameter is any one of either $SpO_2$, $SaO_2$, $PaO_2$, or $CaO_2$. An example of a sensor that measures $SpO_2$ is a conventional pulse oximeter, and a sensor that measures $SaO_2$, $PaO_2$, or $CaO_2$ is a continuous indwelling catheter. Depending on the parameter measured, a conversion to $XaO_2$ may be necessary. This can be done, for example, by microprocessor 36. In the embodiment illustrated in FIG. 12, the pulse oximeter includes a pulse oximeter sensor 39 in contact with the patient to measure the oxygen saturation $SpO_2$ of patient 37.

The present invention contemplates that cardiac output measurement device 30 includes an input/output interface 40 for communicating with the user. For example, a display or other indicator may be provided that notifies the user when to induce that change in arterial oxygen concentration, as well as outputs the cardiac measurement result. A communication link 42 can also be provided for downloading or receiving information and commands to or from a remote location.

One embodiment of the present invention contemplates that one or more of the patient flow measurement system, the oxygen analyzing system, and the fractional arterial oxygen concentration measuring system can be implemented in a separate, stand-alone, module with the output of each being provided to processor 36. This enables different types of patient flow, oxygen analyzing, and arterial oxygen concentration measuring systems to be used with a common cardiac output determination module. One benefit being that existing patient flow sensors, oxygen analyzers, and arterial oxygen concentration measuring systems, such as a conventional pulse oximeter, can be used to provide the required inputs to the cardiac output module.

However, the present invention also contemplates that the patient flow measuring system, the oxygen analyzing system, and arterial oxygen concentration measuring system, or any combination thereof, can be integrated into a single housing 43, as shown, for example, in FIG. 12. In this embodiment, the measuring elements of each system, such as the flow element 33, the airway adapter and $O_2$ transducer 35, and the pulse oximeter sensor 39, provide inputs, e.g., electronic, optical, pneumatic, or otherwise, to one or more processing systems in housing 43.

Also necessary for purposes of the present invention, as shown in FIG. 12, is a device or technique, generally indicated at 50, for inducing a change in the patient's arterial oxygen concentration. In the illustrated exemplary embodiment, device 50 is a rebreathing system that captures the patient's expired gas in a collection reservoir 52. A valve 54 controls the flow of gas, so that when the cardiac output system is not actuated, the patient's airway communicates with ambient atmosphere or a conventional ventilator or pressure support system (not shown). In this embodiment, when the cardiac output is to be measured, valve 54 is controlled manually or via processor 36, to cause the patient's exhaled gas to be delivered to reservoir 52 where it is collected. Because the gas collected in reservoir 52 has been exhaled by the patient, its oxygen concentration is significantly reduced.

In a further embodiment of the present invention, a device 56 for removing $CO_2$ is included in rebreathing system 50, so that the spontaneously breathing patient does not rebreathe significant amounts of $CO_2$. In a preferred embodiment of the present invention, device 56 is a $CO_2$ scrubber that removes $CO_2$ from the gas passing therethrough. As noted above, for a non-spontaneously breathing patient, $CO_2$ removal device 56 is optional, because their breathing pattern is controlled by the ventilator regardless of the $CO_2$ levels inhaled by the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method for measuring cardiac output comprising:
   (1) quantitatively measuring a first parameter indicative of a patient's oxygen uptake and a second parameter indicative of such a patient's fractional arterial oxygen concentration;
   (2) inducing a change in such a patient's arterial oxygen concentration;
   (3) repeating the airflow, the first parameter and the second parameter measurements set forth in step (1); and
   (4) determining an estimate of the patient's cardiac output based on the first parameter and the second parameter information collected in steps (1) and (3).

2. The method according to claim 1, wherein the second parameter indicative of fractional arterial oxygen concentration is one of $SaO_2$, $PaO_2$, $CaO_2$ or $SpO_2$.

3. The method according to claim 1, wherein measuring the airflow includes providing a flow sensor proximate to such a patient's airway, wherein the flow sensor outputs a flow signal indicative of a flow of breathing to or from such a patient.

4. The method according to claim 1, wherein measuring the first parameter includes providing an oxygen analyzing element proximate to such a patient's airway, wherein the oxygen analyzing element outputs an oxygen concentration signal indicative of an amount of oxygen in gas passing through the oxygen sensor.

5. The method according to claim 1, wherein measuring the second parameter includes providing a pulse oximeter sensor in contact with such a patient, wherein the pulse oximeter sensor outputs a signal indicative of an oxygen saturation $SaO_2$ of such a patient.

6. The method according to claim 1, wherein inducing a change in such a patient's arterial oxygen concentration includes introducing a non-oxygen breathing gas into a stream of gas to be inhaled by such a patient or introducing oxygen into the stream of gas to be inhaled by such a patient.

7. The method according to claim 1, wherein inducing a change in such a patient's arterial oxygen concentration includes rebreathing gas exhaled by such a patient.

8. The method according to claim 7, wherein rebreathing includes removing carbon dioxide $CO_2$ from the exhaled gas before the exhaled gas is rebreathed.

9. The method according to claim 1, wherein determining an estimate of the patient's cardiac output includes:
   determining a deviation of such a patient's oxygen uptake from a baseline oxygen uptake level occurring responsive to the induced change in such a patient's arterial oxygen concentration in step (2);
   determining a deviation of such a patient's arterial oxygen concentration from a baseline arterial oxygen concentration level occurring responsive to the induced change in such a patient's arterial oxygen concentration in step (2); and
   comparing the deviation in oxygen uptake to the deviation in arterial oxygen concentration.

10. The method according to claim 9, wherein determining the deviation of such a patient's oxygen uptake includes determining an effective area between the baseline oxygen uptake level and an oxygen uptake curve occurring responsive to the execution of step (2), and wherein determining the deviation of such a patient's arterial oxygen concentration includes determining an effective area between the baseline arterial oxygen concentration level and an arterial oxygen concentration curve occurring responsive to the execution of step (2).

11. The method according to claim 9, wherein determining the deviation of such a patient's oxygen uptake includes determining a slope of a line extending between the baseline oxygen uptake level and a point on an oxygen uptake curve occurring responsive to the execution of step (2), and wherein determining the deviation of such a patient's arterial oxygen concentration includes determining a slope of a line extending between the baseline arterial oxygen concentration level and a point on an arterial oxygen concentration curve occurring responsive to the execution of step (2).

12. The method according to claim 9, wherein determining the deviation of such a patient's oxygen uptake includes determining a magnitude between the baseline oxygen uptake level and a point on an oxygen uptake curve occurring responsive to the execution of step (2), and wherein determining the deviation of such a patient's arterial oxygen concentration includes determining a magnitude between the baseline arterial oxygen concentration level and a point on an arterial oxygen concentration curve occurring responsive to the execution of step (2).

13. The method according to claim 1, further comprising outputting, in human perceivable form, an indication of the cardiac output determined in step (4).

14. An apparatus for measuring cardiac output comprising:
   means for measuring a first parameter indicative of a patient's oxygen uptake; means for measuring a second parameter indicative of such a patient's fractional arterial oxygen concentration;
   means for inducing a change in such a patient's arterial oxygen concentration;
   a processor adapted to determine an estimate of such a patient's cardiac output based on the output of the first parameter and the second parameter; and
   outputting means for outputting a result indicative of such a patient's cardiac output in human perceivable form.

15. The apparatus according to claim 14, wherein the means for measuring the second parameter is a pulse oximetry system including a pulse oximeter sensor in contact with such a patient.

16. The apparatus according to claim 14, wherein the second parameter indicative of fractional arterial oxygen concentration is one of $SaO_2$, $PaO_2$, $CaO_2$ or $SpO_2$.

17. The apparatus according to claim 14, wherein the patient flow measuring system includes a flow sensor disposed proximate to such a patient's airway such that gas inhaled and exhaled by the patient passes through the flow sensor.

18. The apparatus according to claim 14, wherein the oxygen analyzing system includes an oxygen analyzing element comprising (a) an airway adapter having an optical window and (b) an oxygen transducer having an photoemitter and a photodetector, and wherein the oxygen analyzing element is disposed proximate to such a patient's airway such that gas inhaled and exhaled by such a patient passes in front of the optical window.

19. The apparatus according to claim 14, wherein the means for inducing a change in such a patient's arterial oxygen concentration comprises a system for introducing a non-oxygen breathing gas into a stream of gas to be inhaled by such a patient or a system for introducing oxygen into the stream of gas to be inhaled by such a patient.

20. The apparatus according to claim 14, wherein the means for inducing a change in such a patient's arterial oxygen concentration comprises a rebreathing system for causing such a patient to rebreathe gas exhaled by such a patient.

21. The apparatus according to claim 20, wherein the rebreathing system further comprises means for removing carbon dioxide $CO_2$ from the exhaled gas before the exhaled gas is rebreathed.

22. The apparatus according to claim 14, wherein the processor determines:
   (a) a deviation of such a patient's oxygen uptake from a baseline oxygen uptake level occurring responsive to an induced a change in such a patient's arterial oxygen concentration;
   (b) a deviation of such a patient's arterial oxygen concentration from a baseline arterial oxygen concentration level occurring responsive to an induced a change in such a patient's arterial oxygen concentration; and
   (c) a comparison the deviation in oxygen uptake to the deviation in arterial oxygen concentration.

23. The apparatus according to claim 22, wherein the processor determines the deviation of such a patient's oxygen uptake by determining an effective area between the baseline oxygen uptake level and an oxygen uptake curve occurring responsive to the induced change in such a patient's arterial oxygen concentration, and determines a deviation of such a patient's arterial oxygen concentration by determining an effective area between the baseline arterial oxygen concentration level and an arterial oxygen concentration curve occurring responsive to the induced change in such a patient's arterial oxygen concentration.

24. The apparatus according to claim 22, wherein the processor determines the deviation of such a patient's oxygen uptake by determining a slope of a line extending between the baseline oxygen uptake level and a point on an oxygen uptake curve occurring responsive to the induced change in such a patient's arterial oxygen concentration, and determines the deviation of such a patient's arterial oxygen concentration by determining a slope of a line extending between the baseline arterial oxygen concentration level and a point on an arterial oxygen concentration curve occurring responsive to the induced change in such a patient's arterial oxygen concentration.

25. The apparatus according to claim 22, wherein the processor determines the deviation of such a patient's oxygen uptake by determining a magnitude between the baseline oxygen uptake level and a point on an oxygen uptake curve occurring responsive to the induced change in such a patient's arterial oxygen concentration, and determines the deviation of such a patient's arterial oxygen concentration by determining a magnitude between the baseline arterial oxygen concentration level and a point on an arterial oxygen concentration curve occurring responsive to the induced change in such a patient's arterial oxygen concentration.

* * * * *

UNITED STATES PATENT AND TRADEMARK OFFICE
CERTIFICATE OF CORRECTION

PATENT NO. : 6,699,203 B2
DATED : March 2, 2004
INVENTOR(S) : Starr et al.

It is certified that error appears in the above-identified patent and that said Letters Patent is hereby corrected as shown below:

Column 16,
Line 9, delete "airflow, the".

Signed and Sealed this

Twenty-seventh Day of July, 2004

JON W. DUDAS
*Acting Director of the United States Patent and Trademark Office*